United States Patent
Bickham et al.

(10) Patent No.: US 7,153,480 B2
(45) Date of Patent: Dec. 26, 2006

(54) APPARATUS FOR AND METHOD OF PRODUCING AROMATIC CARBOXYLIC ACIDS

(76) Inventors: David Robert Bickham, 8 Berkely Drive Guisborough, Cleveland (GB) TS14 7LX; Michael Cooke, 42 Hall Avenue, Cheshire (GB) WA8 8XS; Martin Reid Burton Davis, The White House Hutton Village Road Guisborough, Cleveland (GB) TS14 8EJ; Samuel Duncan Housley, 5 Blue Barn Lane Hutton Rudby, Yarm, North Yorkshire (GB) TS15 0JG; Finbar Gerald McDonnell, 57 Falcon Way Guisborough, Cleveland (GB) TS14 8HT (*) Notice: Subject to any disclaimer, the term of this patent is extended or adjusted under 35 U.S.C. 154(b) by 393 days.

(21) Appl. No.: 10/443,542

(22) Filed: May 22, 2003

(65) Prior Publication Data
US 2004/0234435 A1    Nov. 25, 2004

(51) Int. Cl.
*B01J 19/18* (2006.01)
(52) U.S. Cl. ............. 422/224; 422/225; 422/229; 562/412; 562/414; 366/327; 366/330
(58) Field of Classification Search ............. 422/224, 422/225, 229; 562/412, 414; 366/325, 327, 366/330
See application file for complete search history.

(56) References Cited

U.S. PATENT DOCUMENTS

| | | | | |
|---|---|---|---|---|
| 4,438,074 A | * | 3/1984 | Wilt ............................ | 422/135 |
| 4,610,547 A | | 9/1986 | Bennett et al. | |
| 4,779,990 A | | 10/1988 | Hjort et al. | |
| 4,935,539 A | * | 6/1990 | Lee ............................ | 562/412 |
| 5,099,064 A | * | 3/1992 | Huber et al. ................ | 562/414 |
| 5,102,630 A | * | 4/1992 | Lee ............................ | 422/224 |
| 5,198,156 A | | 3/1993 | Middleton et al. | |
| 5,211,924 A | * | 5/1993 | Lee et al. ................... | 422/225 |
| 5,320,500 A | * | 6/1994 | Cholet ........................ | 417/375 |
| 5,536,875 A | * | 7/1996 | Roby et al. ................. | 562/412 |
| 6,024,481 A | * | 2/2000 | Hillstrom et al. .......... | 366/155.1 |
| 2004/0062144 A1 | * | 4/2004 | Hultholm et al. ........... | 366/317 |
| 2004/0254397 A1 | * | 12/2004 | Varela-Fuentes et al. ... | 562/412 |

FOREIGN PATENT DOCUMENTS

| | | |
|---|---|---|
| EP | 0 988 105 B | 8/1992 |
| EP | 0 659 730 A | 6/1995 |
| EP | 0 781 754 A | 7/1997 |
| JP | 10316614 | 2/1998 |
| JP | 2000128824 | 9/2000 |
| WO | WO 02/092549 | 11/2002 |

* cited by examiner

*Primary Examiner*—N. Bhat
(74) *Attorney, Agent, or Firm*—Charles E. Krukiel

(57) ABSTRACT

A reactor for the oxidation of a precursor to an aromatic carboxylic acid or ester thereof in a liquid phase reaction mixture is disclosed. The reactor comprises an elongate vessel, substantially vertical in use, having an upper mixing element and a lower mixing element, characterised in that the upper mixing element is an axial pumping impeller and the lower mixing element is a radial pumping impeller. A process of producing a carboxylic acid or ester thereof in a reactor of the invention is also disclosed. In use, the configuration of mixing elements leads to three highly turbulent mixing zones. In a preferred embodiment of the process of the present invention oxidant, from one inlet, and solvent, precursor and catalyst, are introduced directly into a mixing zone. The highly turbulent mixing zones lead to rapid mass transfer suppressing the formation of unwanted, coloured by-products and reduced reactor fouling.

22 Claims, 6 Drawing Sheets

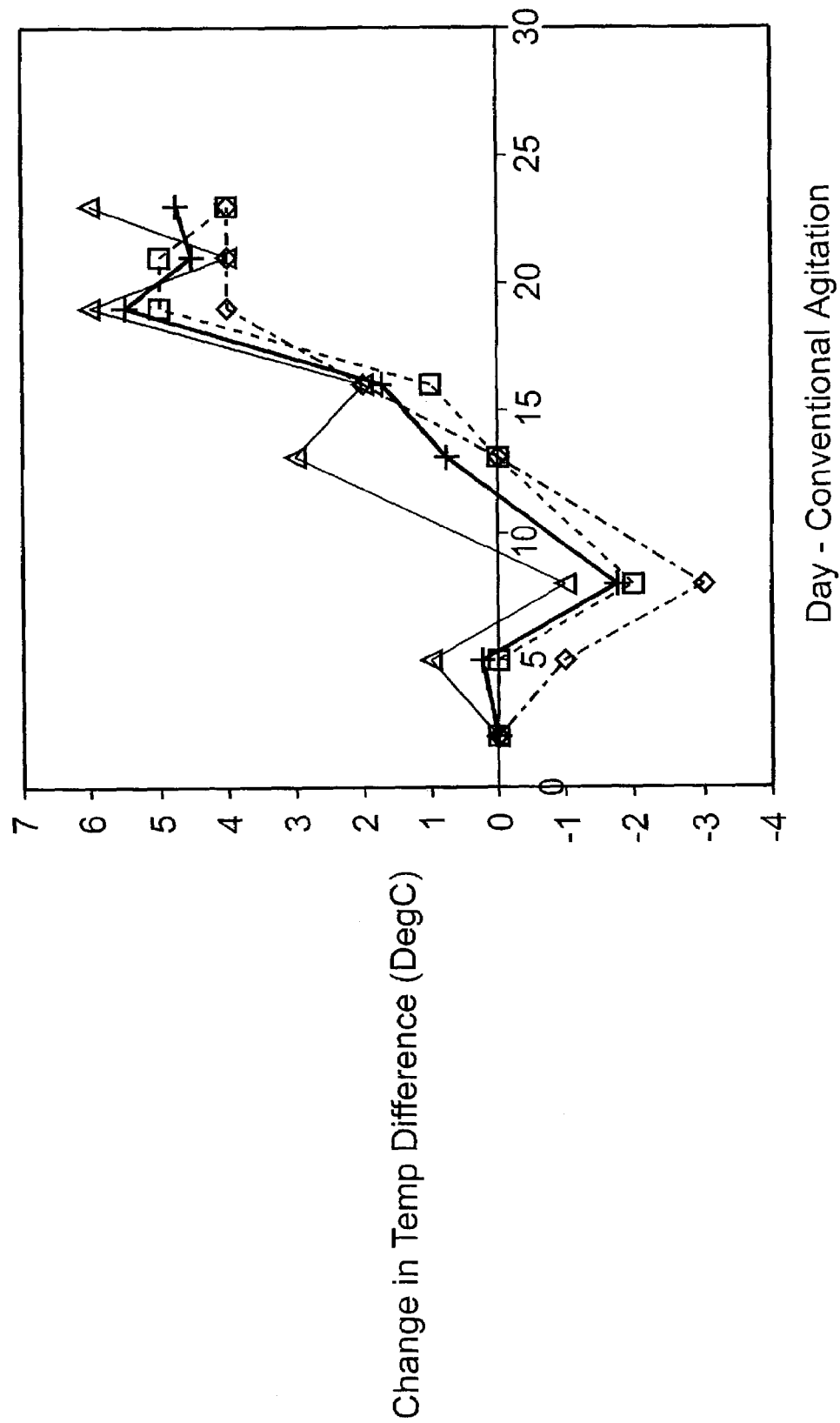
Fig. 5 'A' Reactor Temp Differences

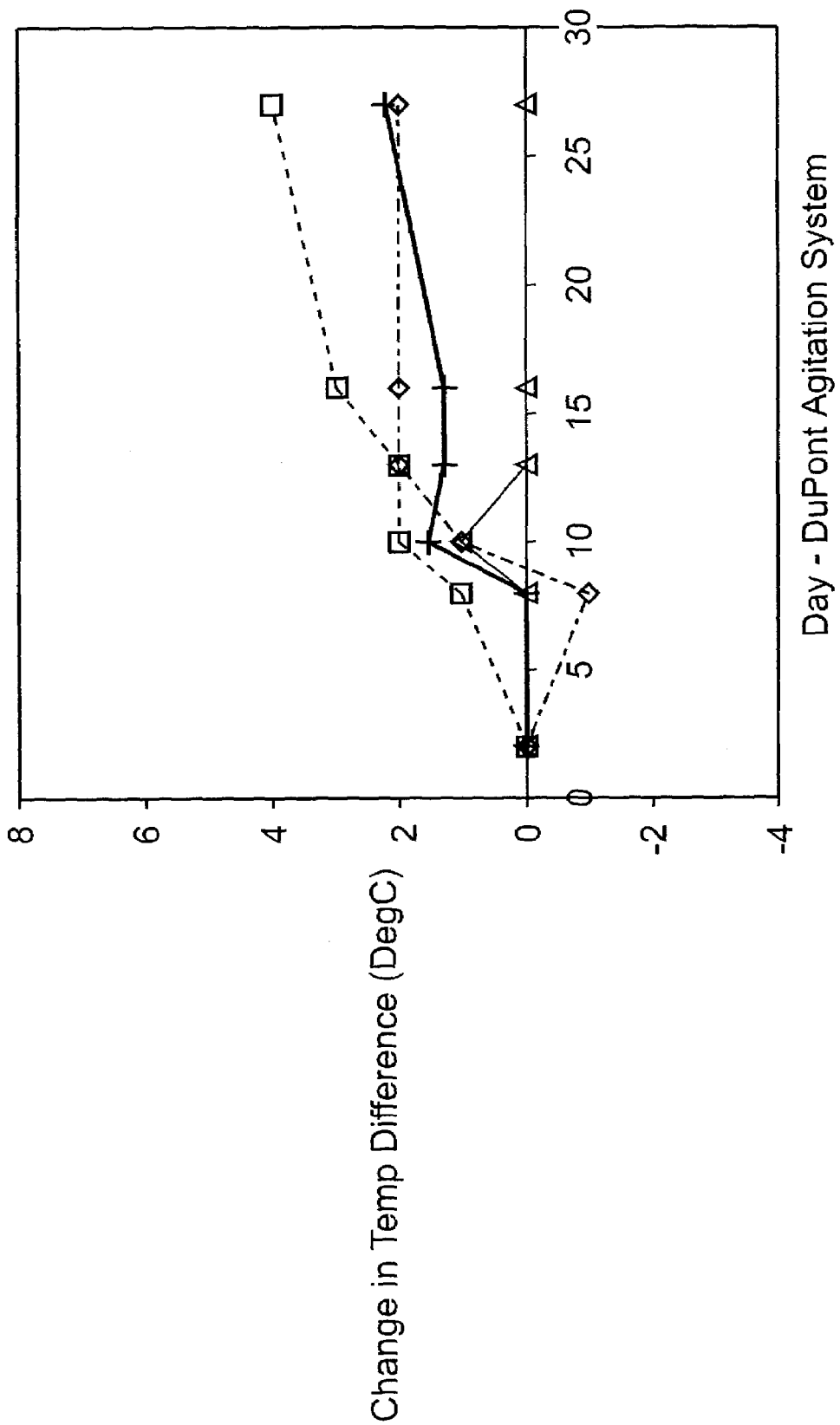
Fig. 6 'A' Reactor Temp Differences

APPARATUS FOR AND METHOD OF PRODUCING AROMATIC CARBOXYLIC ACIDS

TECHNICAL FIELD

This invention relates to an apparatus for producing aromatic carboxylic acids, particularly di-carboxylic acids, or their esters by catalytic liquid phase oxidation of a corresponding precursor. In particular, the invention relates to apparatus for producing aromatic carboxylic acids of low impurity content. The invention further extends to a process of producing aromatic carboxylic acids or their esters by catalytic liquid phase oxidation of a corresponding precursor. This invention particularly relates to the production of terephthalic acid.

BACKGROUND OF THE INVENTION

Terephthalic acid (TPA) is an important chemical intermediate which is used for the production of industrially significant products, including polyester polymers which can be used for fibre production and in the manufacture of bottles.

Current technology for the manufacture of terephthalic acid involves the liquid phase oxidation of paraxylene feedstock using molecular oxygen in a lower (e.g. $C_2$–$C_6$) aliphatic monocarboxylic acid, usually acetic acid, in the presence of a dissolved heavy metal catalyst system usually incorporating a promoter, such as bromine. In general, acetic acid, molecular oxygen in the form of air, paraxylene and catalyst are fed continuously into an oxidation reactor at elevated temperature and pressure. Air is added in amounts in excess of the stoichiometric requirements for full conversion of the paraxylene to TPA, to minimise formation of undesirable by-products, such as colour formers. The oxidation reaction is exothermic, and heat is removed by allowing the acetic acid solvent to vaporise. The corresponding vapor is condensed and most of the condensate is refluxed to the reactor, with some condensate being withdrawn to control reactor water concentration (two moles of water are formed per mole of paraxylene reacted).

The effluent, i.e. reaction product, from the oxidation reactor is a slurry of crude TPA crystals which are recovered from the slurry by filtration, washed, dried and conveyed to storage. The crystals are thereafter fed to a separate purification step or directly to a polymerisation process.

Generally, however, the terephthalic acid obtained is not sufficiently pure for direct use in polyester production since it contains, as major impurities, partially oxidised intermediates of terephthalic acid, particularly 4-carboxybenzaldehyde (4-CBA), although also p-tolualdehyde and p-toluic acid, along with other various colour-forming precursors and coloured impurities.

It is known that poor mixing in the oxidation reactor leads to undesirably high levels of the above-mentioned impurities in the final TPA product. An additional problem in the oxidation reactor is that detailed design features and operating conditions, e.g., temperature, catalyst concentration and residence time, can cause significant degradation of the solvent and precursor, which, in turn, can increase the cost of the operating process. A further important feature of the oxidation reactor is that solid crystals of crude TPA formed in the reactor must be adequately suspended to prevent choking of vessel walls and pipelines which in turn leads to unsafe operation of the process and frequent interruption for cleaning.

Vigorous agitation is known to reduce the above problems and Japanese patent no. 10316614 describes a multi-impeller agitator with the lower paddles larger than the upper paddles. However, such a system suffers from high initial cost and high operating cost. U.S. Pat. No. 5,211,924 describes a multi-agitator system in which the paddle type, size and location in the oxidation reactor reduce operating costs and reduce levels of impurity in the TPA product.

An alternative approach to reducing the levels of impurities in the crude TA product formed in the oxidation reactor has been to disperse the air and liquid feeds to the reactor more uniformly. JP 2000128824 describes a reactor whereby liquid feed is dispersed through a plurality of nozzles in the reactor, located at various points across the diameter or vertical height of the reactor, and matched with the flow of oxygen throughout the reactor. Such an arrangement prevents high concentrations of liquid feed, such high concentration being known to cause higher impurity formation. However, such a process is complex, the reactor is costly to fabricate and does not solve the problem of solid suspension.

WO02/092549 discloses an agitation system for TPA oxidation reactors consisting of an asymmetric radial turbine in combination with one or more down-pumping axial impellers. However, this potentially results in foaming in the reaction mixture which can result in carryover of reaction mixture into the reactor headspace and overheads equipment which leads to fouling and other operating problems.

It is therefore an object of this invention to provide an apparatus for producing TPA having decreased amounts of impurities, particularly coloured impurities. It is a further object of this invention to provide an apparatus having low equipment cost and low operating cost. It is a still further object of this invention to provide an apparatus in which the produced TPA is suspended in the solvent to prevent choking of the apparatus.

SUMMARY OF THE INVENTION

In a first aspect of the invention, there is provided a reactor for the oxidation of a precursor to an aromatic carboxylic acid or ester thereof in a liquid phase reaction mixture, the reactor comprising an elongate baffled vessel, substantially vertical in use, having an upper mixing element and a lower mixing element, characterised in that the upper mixing element is an axial up-pumping impeller and the lower mixing element is a radial pumping impeller.

In a second aspect of the invention, there is provided a process of oxidising a precursor to an aromatic carboxylic acid or ester thereof in a liquid phase reaction mixture, comprising contacting one or more precursors of the aromatic carboxylic acid with an oxidant, in the presence of a catalyst and a liquid phase solvent, said contacting being effected in a reactor comprising an elongate baffled vessel, substantially vertical in use, having an upper mixing element and a lower mixing element, characterised in that the upper mixing element is an axial up-pumping impeller and the lower mixing element is a radial pumping impeller.

The configuration of the mixing elements in the reactor of the present invention leads, in use, to three mixing zones, two lower mixing zones, one above and one below the lower impeller, and a third upper mixing zone above and below the upper impeller. The mixing zones are defined by interfaces formed by local converging or diverging flow as shown in FIG. 4. Without prejudice to the scope of the present invention, it is believed that the above-mentioned mixing zones enable rapid mass transfer of oxidant. The rapid mass transfer minimises by-product formation and reduces degradation of solvent and precursor and hence improves product quality and process efficiency.

Moreover, this configuration provides a mixing regime in the reactor so as to prevent coating of vessel walls and pipelines and, in particular, minimise fouling in the lower part of the vessel.

DETAILED DESCRIPTION OF THE INVENTION

The present invention relates to a reactor and process which surprisingly improves the conversion of one or more precursors (e.g. paraxylene) to an aromatic carboxylic acid (e.g. terephthalic acid) leading to improved product quality. While the present invention is suitable for producing any aromatic carboxylic acid from a suitable precursor, the production of a di-carboxylic acid, e.g. terephthalic acid and isophthalic acid, is, in particular, contemplated. The aromatic carboxylic acid obtained from the method of the present invention is generally in the form of a slurry.

As used herein, reference to the production of a carboxylic acid includes reference to the production of its ester. As will be evident to the skilled person, whether a carboxylic acid or its ester is produced will depend on the conditions in the reactor and/or the conditions used to purify the products.

As used herein, "aromatic carboxylic acid precursor" or "precursor" means an organic compound, preferably a hydrocarbon, capable of being oxidised to a specific aromatic carboxylic acid in a majority yield in the presence of selective oxidising conditions. An example of a terephthalic acid precursor is paraxylene. An example of an isophthalic acid precursor is metaxylene.

The reactor of the invention comprises two or more, preferably four or more baffles. As used herein, a "baffle" refers to an elongate plate extending radially inwardly from the vessel wall, so as to induce turbulence in the reaction mixture on rotation thereof by the mixing elements.

While any "axial up-pumping impeller" used in the reactor of the present invention would suffice, best results have been obtained with an up-pumping impeller in which the blade makes an angle of less than 90 degrees with the plane of rotation. Preferably, the up-pumping impeller is a pitched blade turbine provided with two or more, preferably between 4 and 8 and more preferably, 6, equally spaced blades disposed at an angle from the plane of rotation of the impeller of between 30 and 60 degrees, preferably about 45 degrees to provide an up-pumping flow of reaction mixture in the vicinity of the impeller.

An important parameter of the upper mixing element is the swept diameter, i.e. twice the distance between the centre of the shaft and the outer point of a blade of the mixing element. The ratio of the swept diameter to vessel diameter should preferably be from 0.3 to 0.7 and more preferably 0.4 to 0.6. A further important parameter of the upper mixing element is the submergence of the element, the submergence being the distance between the centre of the impeller and the normal operating level of the reaction mixture in the reactor. The ratio of submergence to swept diameter should preferably be from 0.6 to 1.2.

While any "radial pumping impeller" used in the reactor of the present invention is suitable, best results have been obtained with a radial impeller in which the blade is parallel to the axis of rotation. Preferably, the impeller has equally spaced, curved blades, in particular curved, parabolic blades with a plane of symmetry which is parallel to the plane of rotation. The radial impellers disclosed in U.S. Pat. No. 5,198,156 (known as Gasfoil impellers) and U.S. Pat. No. 4,779,990 are particularly preferred.

An important parameter of the lower mixing element is the swept diameter, i.e. twice the distance between the centre of the shaft and the outer point of a blade of the mixing element. The ratio of the swept diameter to vessel diameter should be preferably be from 0.4 to 0.6 and more preferably 0.45 to 0.55. A further important parameter of the lower mixing element is the clearance from the base of the vessel, i.e. the distance from the base of the vessel to the centre of the lower mixing element. The ratio of the clearance from the base of the vessel to the vessel diameter should preferably be from 0.1 to 1.0.

An important parameter of the reactor is the separation between the lower mixing element and the upper mixing element, i.e. the distance between the centre of the lower mixing element and the centre of the upper mixing element. Preferably, the ratio of the separation between the lower mixing element and the upper mixing element to the swept diameter of the lower mixing element is between 0.6 to 1.2.

The reactor may comprise one or more further agitator elements for mixing the contents of the reactor. The upper and lower mixing elements, and any further agitator elements, may be connected to one or more axial shafts. Typically, the axial shafts pass through the centre-line of the vessel.

Preferably, the reactor comprises an oxidant inlet having one or more inlet mouths for introducing an oxidant into the reactor. The oxidant is preferably gaseous and more preferably molecular oxygen. Preferably, the or each oxidant inlet mouth is disposed such that in use oxidant is introduced directly into a highly turbulent region of a mixing zone, preferably a lower mixing zone. Still more preferably, the reactor comprises two or more oxidant inlets, the mouths of each of which are disposed such that in use oxidant is introduced from each mouth directly into a highly turbulent region of a mixing zone, preferably a lower mixing zone. Introducing the oxidant into a highly turbulent region of a mixing zone causes gaseous oxidant to be broken into fine bubbles. Accordingly, well-dispersed gaseous oxidant is introduced into the reactor thereby providing rapid mass transfer of oxygen into the reaction mixture minimising by-product formation and hence improving product quality and process efficiency.

In order to ensure that an oxidant inlet mouth is disposed such that in use oxidant is introduced directly into a highly turbulent region of a lower mixing zone, the oxidant inlet mouth is preferably located below the plane of the upper surface of the lower impeller, preferably between the plane of the upper surface of the lower impeller and the plane of the lower surface of the lower impeller, and still more preferably between the centre of the lower impeller and the plane of the lower surface of the lower impeller. Preferably, the oxidant inlet mouth is located between the swept diameter of the lower mixing element and the vessel wall. More preferably, the oxidant inlet mouth is located such that the ratio of the distance between the swept diameter of the lower mixing element (illustrated in FIG. 3 as distance (a)) and the wall of the inlet mouth to the vessel diameter (illustrated as distance (T) in FIG. 3) is in the range of ratio of 0.02 to 0.08, preferably 0.04 to 0.06.

Types of inlet for feeding oxidant into the oxidation reactor are well known in the art. However, it is preferable that the direction of oxidant ingress into the reaction mixture is not opposite to the direction of mixing element rotation.

The location of the mouths of the oxidant inlets with respect to the mouths of the liquid inlets and around the vessel circumference for multi air feed points is preferably equispaced and beyond (in terms of the direction of rotation of the agitator) the nearest adjacent baffle.

Preferably, the reactor comprises one or more liquid inlets, each having mouths, for introducing, preferably simultaneously, a liquid feed of solvent, precursor and catalyst into the reactor. Preferably, the liquid feed also includes condensate produced from vapour generated within the reactor, as described below. The liquid feed may also include various impurities, including by-products of the oxidation process and crude aromatic carboxylic acid.

Preferably, the or each liquid feed inlet mouth is disposed such that in use liquid feed is introduced into a region where reaction mixture is induced to flow into a mixing zone, preferably a lower mixing zone. Introducing the liquid feed into a mixing zone leads to rapid mixing of reactants, minimising by-product formation and hence improving product quality and process efficiency.

In a first preferred embodiment, the or each liquid feed inlet mouth is disposed such that in use liquid feed is introduced directly into one or more highly turbulent regions of one or both lower mixing zones. In this embodiment, the or each liquid inlet mouth is located between the plane of the upper surface of the lower impeller and the plane of the lower surface of the lower impeller, and between the swept diameter of the lower mixing element and the vessel wall. Preferably, the or each liquid inlet mouth is located equidistant between the plane of the upper surface of the lower impeller and the plane of the lower surface of the lower impeller. Preferably, the liquid inlet mouth is located about equidistant from the swept diameter of the mixing element and the vessel wall. Types of inlet for feeding liquid into the oxidation reactor are well known in the art. The location of the liquid inlets is preferably between two adjacent oxidant inlets.

In a second preferred embodiment, the or each liquid feed inlet mouth is disposed such that in use liquid feed is introduced into a region where reaction mixture is induced to flow via a mixing element into a highly turbulent region of a mixing zone, preferably a lower mixing zone. In this embodiment, the or each liquid inlet mouth is located above or below the impeller and within the swept diameter of the impeller. Preferably, the ratio of the distance of the liquid inlet mouth above or below the impeller to the swept diameter of the impeller is less than 0.5.

Preferably, the reactor comprises a vapour outlet for allowing the volatile components in the reactor, particularly the solvent, to be removed from the reactor. Preferably, the volatile compounds are condensed and condensate is refluxed to the reactor.

The reactor preferably comprises an aromatic carboxylic acid outlet. Preferably, the aromatic carboxylic acid outlet is located in the upper mixing zone. Such a location is preferable in order to minimise loss of unreacted precursor and hence improve efficiency and operating costs.

Preferably, the reactor is a continuous flow reactor. As used herein, "continuous flow reactor" means a reactor in which reactants are introduced and mixed and products withdrawn simultaneously in a continuous manner, as opposed to a batch-type reactor. By carrying out the process in a continuous flow reactor, the residence time for the reaction can be made compatible with the attainment of conversion of the precursors to the desired aromatic carboxylic acids without significant production of degradation products. The residence time of the reaction medium within the reactor is typically no more than 20–120 minutes and preferably of the order of 30–60 minutes of oxidising a precursor to an aromatic carboxylic acid or ester thereof in a reactor of the present invention. In the process of the present invention, the reactor is operated such that the upper mixing element induces upward axial flow of the reaction mixture at the upper mixing element. In combination with the radial flow of the lower radial impeller, the upward axial flow of the upper axial impeller provides mixing zones allowing rapid mass transfer of reactants. Additionally, this mixing regime provides good solid (e.g. product aromatic carboxylic acid) suspension and minimum fouling in the lower part of the vessel via the mixing elements.

In order to provide optimal flow in the reaction mixture in the reactor, a power input of 2 to 15 kw per $m^3$ of reaction mixture is imparted to the reaction mixture by the upper mixing element, lower mixing element and any further agitator elements.

Preferably, the power imparted by the upper mixing element is from 10 to 50%, more preferably 30 to 40%, of the power imparted to the reaction mixture by the upper mixing element, lower mixing element and any further agitator elements to the reaction mixture. It has been surprisingly found that such a power distribution leads to improved mixing and the efficient break up of large oxidant bubbles. Such mixing and bubble break-up is able to mass transfer oxidant to the reaction mixture quickly, leading to efficient oxidation in the reactor, and the suppression of coloured intermediates to produce colourless product.

In the process of the invention, the catalytic liquid phase oxidation of precursor to produce aromatic carboxylic acid comprises feeding solvent, oxidant, precursor and catalyst into an oxidation reactor that is maintained at a temperature from 150° C. to 250° C., preferably 175° C. to 225° C., and a pressure from 100 to 5000 kPa, preferably 1000 to 3000 kPa.

The oxidant in the process of the invention is preferably molecular oxygen, e.g. air (including oxygen-depleted air and oxygen enriched air).

The process of the invention is carried out in the presence of an oxidation catalyst. The catalyst is substantially soluble in the reaction medium comprising solvent and the aromatic carboxylic acid precursor(s). The catalyst, typically comprises one or more heavy metal compounds, e.g. cobalt and/or manganese compounds, and may optionally include an oxidation promoter. For instance, the catalyst may take any of the forms that have been used in the liquid phase oxidation of aromatic carboxylic acid precursors such as terephthalic acid precursor(s) in aliphatic aromatic carboxylic acid solvent, e.g. bromides, bromoalkanoates or alkanoates (usually $C_1$–$C_4$ alkanoates such as acetates) of cobalt and/or manganese. Compounds of other heavy metals such as vanadium, chromium, iron, molybdenum, a lanthanide such as cerium, zirconium, hafnium, and/or nickel may be used instead of, or additional to, cobalt and/or manganese. Advantageously, the catalyst system will include manganese bromide ($MnBr_2$) and/or cobalt bromide ($CoBr_2$). The oxidation promoter, where employed, may be in the form of elemental bromine, ionic bromide (e.g. HBr, NaBr, KBr, $NH_4Br$) and/or organic bromide (e.g. bromobenzenes, benzyl-bromide, mono- and di-bromoacetic acid, bromoacetyl bromide, tetrabromoethane, ethylene-di-bromide, etc.).

The solvent is not critical to the present invention and any suitable solvent in which the oxidation can take place may be used. Preferably, the solvent is an aliphatic monocarboxylic acid having from 2 to 6 carbon atoms. More preferably, the solvent is acetic acid. Acetic acid is a particularly useful as the solvent since it is relatively resistant to oxidation in comparison with other solvents and increases the activity of the catalytic pathway.

The oxidation reaction is exothermic and heat may be removed, in order to control the reaction temperature, by removing the volatile components, condensing them, and returning the condensate to the reactor. Alternatively or additionally, the heat of reaction may be removed from the reaction by heat exchange with a heat-accepting fluid, according to conventional techniques known to those skilled in the art.

As mentioned above, the reactor is generally operated in a continuous mode. By carrying out the process in a continuous flow reactor, the residence time for the reaction can be made compatible with the attainment of conversion of the precursors to the desired aromatic carboxylic acids without significant production of degradation products.

The reaction may be effected by heating and pressurising the precursor, catalyst and solvent mixture followed by introduction of the oxidant into the reactor via the oxidant inlet.

The effluent, i.e. reaction product, from the oxidation reactor is generally a slurry of aromatic carboxylic acid crystals which are recovered from the slurry by filtration and subsequent washing. They are thereafter fed to a separate purification step or directly to a polymerization process. The main impurity in crude TPA is 4-carboxybenzaldehyde (4-CBA), which is incompletely oxidized paraxylene, although p-tolualdehyde and p-toluic acid can also be present along with undesirable colour formers.

The invention will now be described further by way of example only with reference to the accompanying drawings in which:

FIG. 5 shows the change in temperature differences between average wall temperature and contents with respect to time in a conventional agitation system.

FIG. 6 shows the change in temperature differences between average wall temperature and contents with respect to time in a agitation system of the invention.

Figure 1:
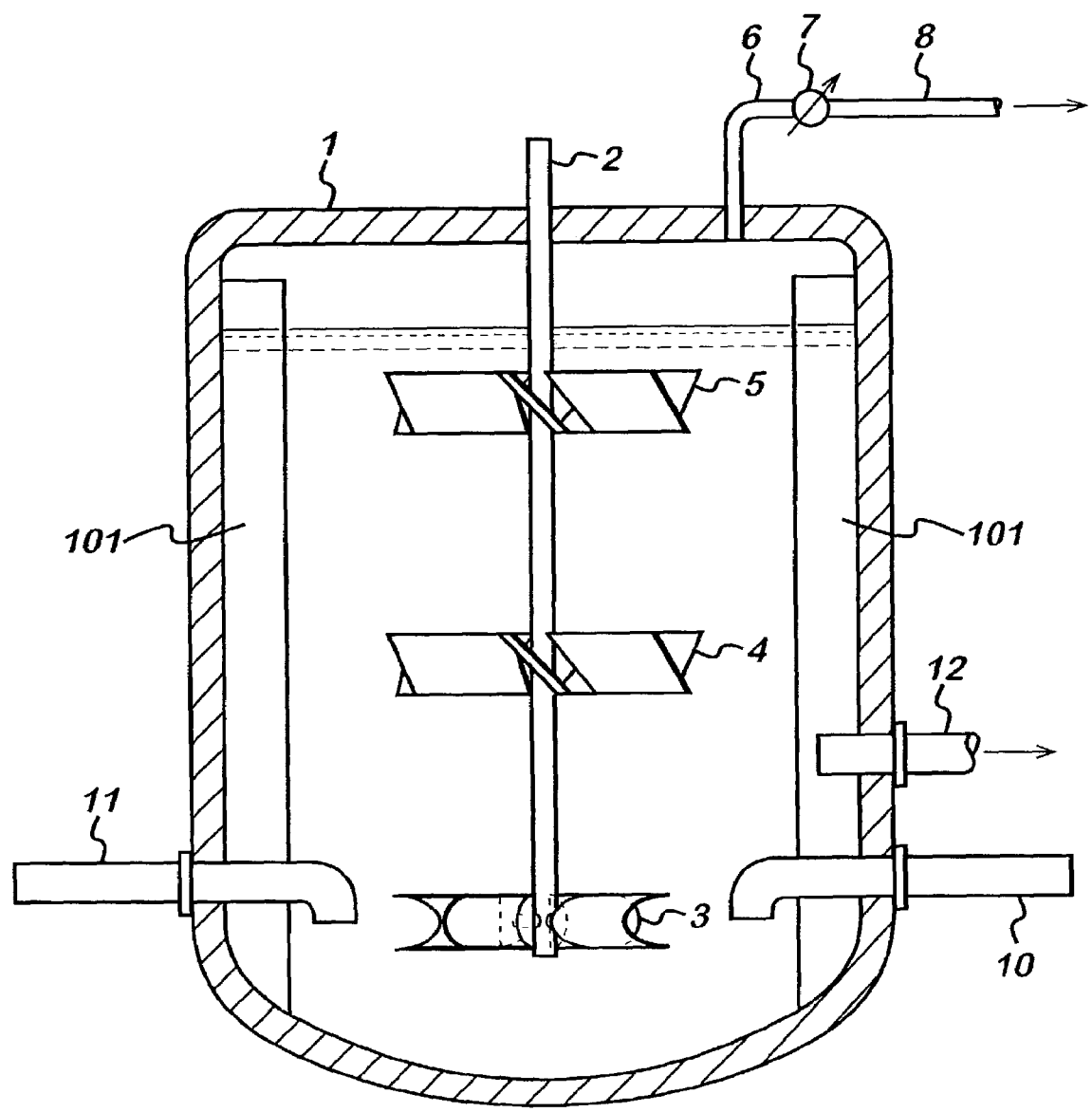
FIG. 1 is a simplified diagram of an oxidation reactor of the present invention.

Oxidation reactor 1 is an elongated, vertically disposed, continuous stirred-tank, vessel having baffles 101 and which includes one or more axial, centrally mounted agitator shaft 2 on which are attached agitator elements 3–5. In this embodiment, elements are shown in order to mix the contents of the reactor and to perform other functions such as spraying liquid onto the reactor walls in order to clean them. The present invention is principally concerned with mixing elements 3 and 4.

In use, the total power imparted thorough the agitator shaft 2 to the contents of the oxidation reactor 1 is from 2 to 15 kW per m³ of reactor slurry. This ensures a mixing regime which possesses the above-mentioned advantages of low reactor fouling, high product quality and high process efficiency.

The lower mixing element 3 is a radial pumping impeller provided with a plurality of equi-spaced blades. However, for best results an agitator as described in U.S. Pat. No. 5,198,156 should be utilised which has parabolic blades with a plane of symmetry which is parallel to the direction of motion. An important parameter of this mixing element is the swept diameter shown as $D_L$ in FIGS. 2 and 3. The swept diameter $D_L$ is twice the distance between the centre of the shaft and the outer point of a blade of the mixing element and it has been discovered that the ratio of swept diameter to vessel diameter T should be from 0.4 to 0.6 and preferably 0.45 to 0.55. A further important parameter is the clearance of the lower mixing element from the base of the vessel $C_L$ and it has been discovered that the ratio of the clearance from the base to vessel diameter T should be from 0.1 to 1.0.

The upper mixing element 4 is an axial up-pumping impeller. Preferably, the upper mixing element is an up-pumping pitched blade turbine provided with a plurality of equi-spaced blades normally angled between 30 and 60 degrees to the horizontal plane and preferably 45 degrees to provide an up pumping flow of slurry within the oxidation reactor. An important parameter of this mixing element is the swept diameter $D_U$ which is twice the distance between the centre of the shaft and the outer point of a blade of the mixing element. It has been discovered that the ratio of swept diameter to vessel diameter T should be from 0.3 to 0.7 and preferably 0.4 to 0.6. A further important parameter is the submergence beneath the normal operating level of slurry in the oxidation reactor s and it has been discovered that the ratio of submergence to swept diameter $D_U$ should be from 0.6 to 1.2. The relative sizing of upper and lower mixing elements is an important parameter and it has been discovered that for best results the upper mixing element should impart 10 to 50% of the total power imparted by all the agitator elements and preferably 30 to 40% of the total power.

Preferably, the ratio of the separation between the lower mixing element and the upper mixing element, i.e. the distance between the centre of the lower mixing element and the centre of the upper mixing element, to the swept diameter of the lower mixing element is between 0.6 to 1.2.

Figure 2:
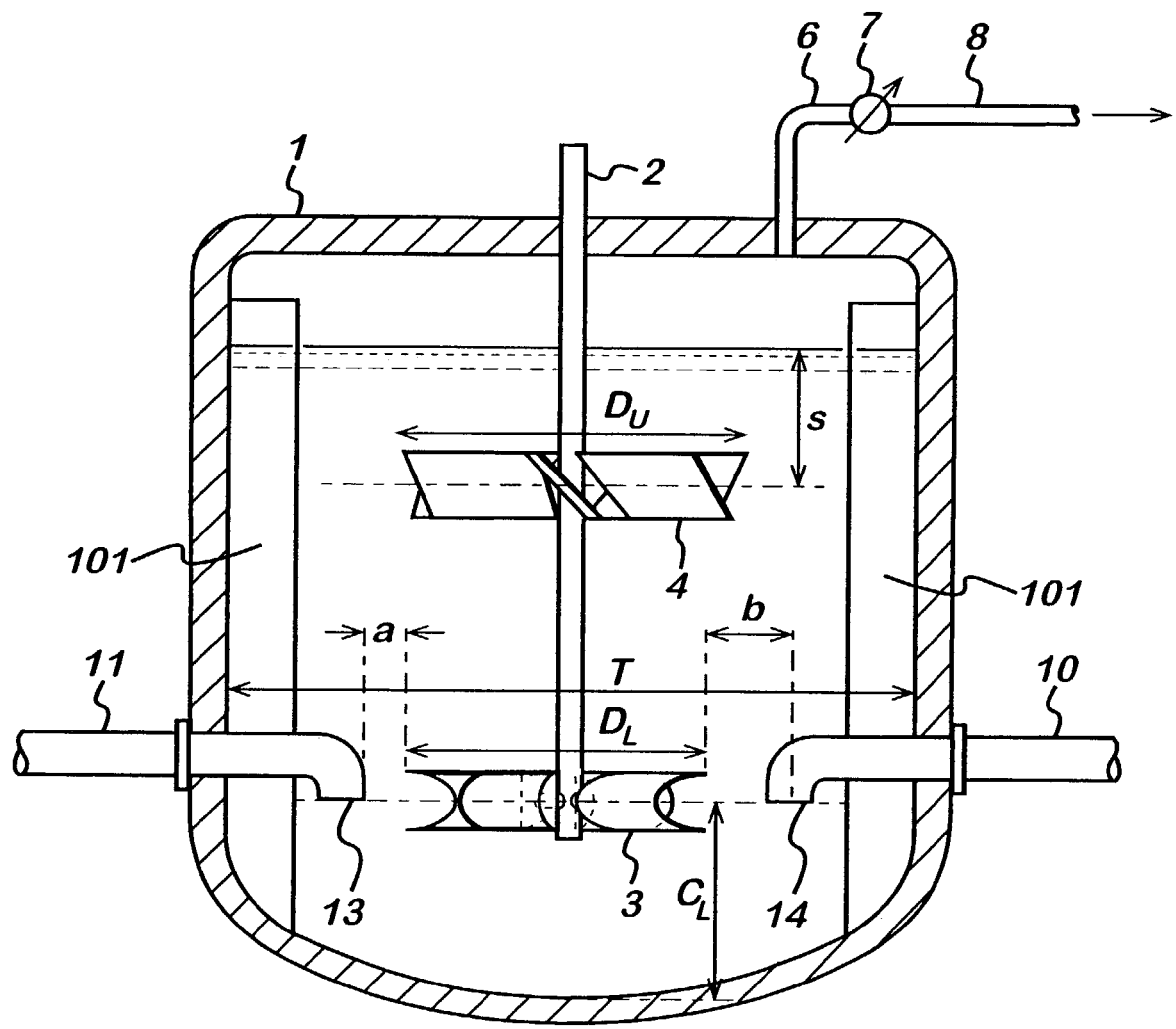
FIG. 2 shows the configuration and position of the features of the reactor of the present invention in a first embodiment where the liquid feed inlet mouth is disposed such that in use liquid feed is introduced directly into a lower mixing zone.

In operation, air is fed into the oxidation reactor in order to oxidize the precursor through one or more inlets 11 each and having inlet mouth 13. Each inlet mouth 13 is located between the plane of the upper surface of the lower mixing element and the plane of the lower surface of the lower mixing element (as shown in FIG. 2) and with a distance from the swept diameter of the lower mixing element a to vessel diameter T ratio of from 0.02 to 0.08 and preferably from 0.04 to 0.06. Methods of feeding air into the oxidation reactor are well known in the art. However, it is preferable that the direction of air ingress into the slurry is not opposite to the direction of agitator rotation.

Liquid feed to the oxidation reactor comprises precursor, catalyst, solvent and condensate along with various impurities and by-products of the crude TA process and is introduced to the reactor via liquid inlets 10, each having inlet mouth 14. The form, composition and source of these streams are well known in the art.

It is important that the major portion of the total liquids as described above are fed to the oxidation reactor via inlet 10 in the one of the two alternative manners described below and preferably that all the liquid is so fed.

In a first preferred embodiment shown in FIG. 2, liquid feed inlet mouth 14 is located between the plane of the upper surface of the lower mixing element and the plane of the lower surface of the lower mixing element and between the swept diameter of the lower mixing element and the vessel wall b and preferably equidistant between the lower mixing element swept diameter and vessel wall. Such a location of the inlet mouth 14 enables liquid feed to be introduced directly into a lower mixing zone.

Figure 3:
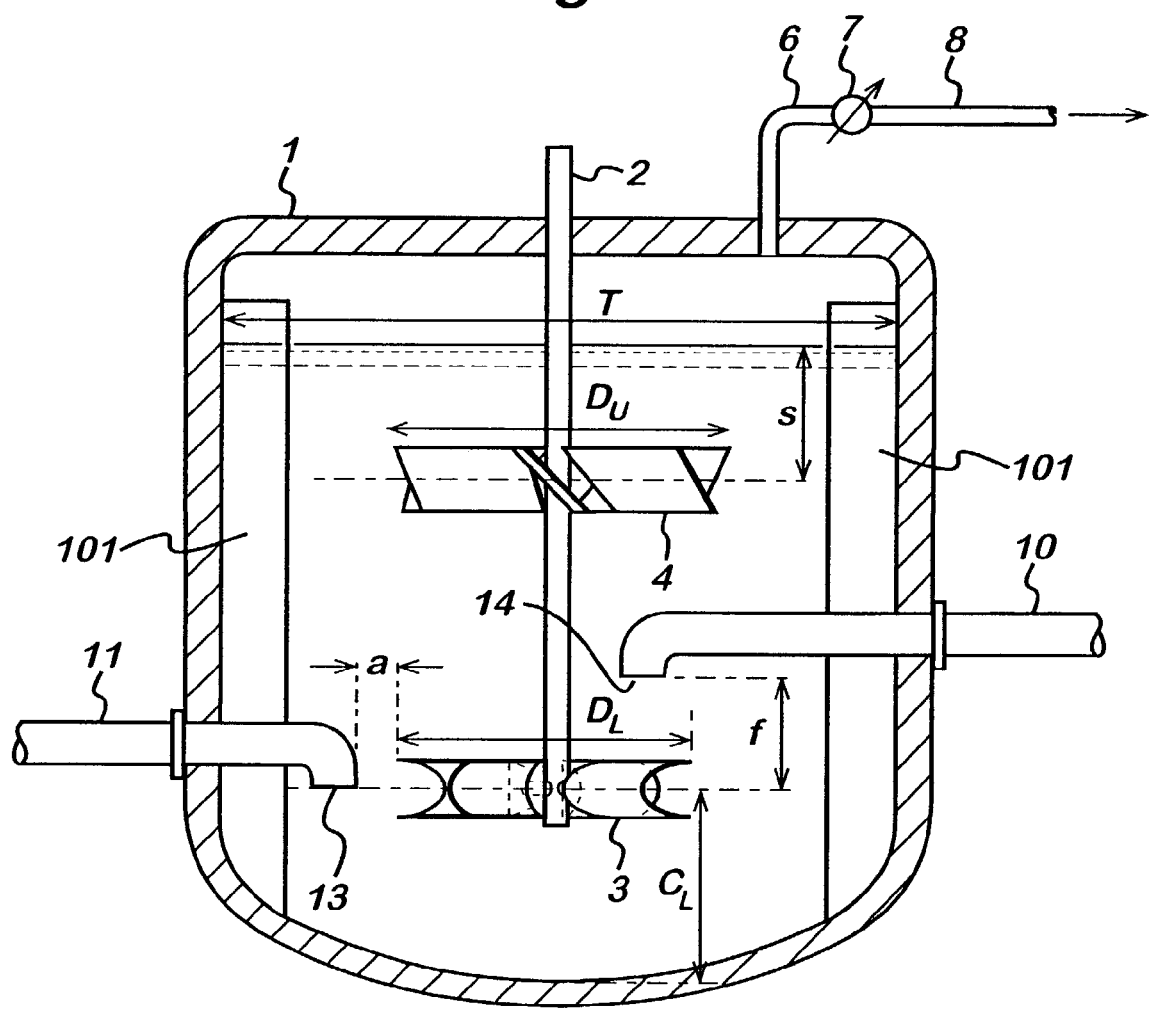
FIG. 3 shows the configuration and position of the features of the reactor of the present invention in a second embodiment where the liquid feed inlet mouth is disposed such that in use liquid feed is introduced into a region where reaction mixture is induced to flow via the lower mixing element into a lower mixing zone.

In a second preferred embodiment shown in FIG. 3, liquid feed inlet mouth 14 is located above the lower mixing element and within the swept diameter of the lower mixing element $D_L$. The ratio of the distance f of the liquid inlet mouth above the mixing element to the swept diameter $D_L$ of the mixing element is generally less than 0.5. As a modification of the second embodiment, liquid feed inlet mouth 14 is located below the lower mixing element and within the swept diameter $D_L$ of the lower mixing element. Such locations of the inlet mouth 14 enable liquid feed to be introduced into a region where reaction mixture is induced to flow, by the motion of the lower mixing element, via the lower mixing element and into a lower mixing zone.

Figure 4:
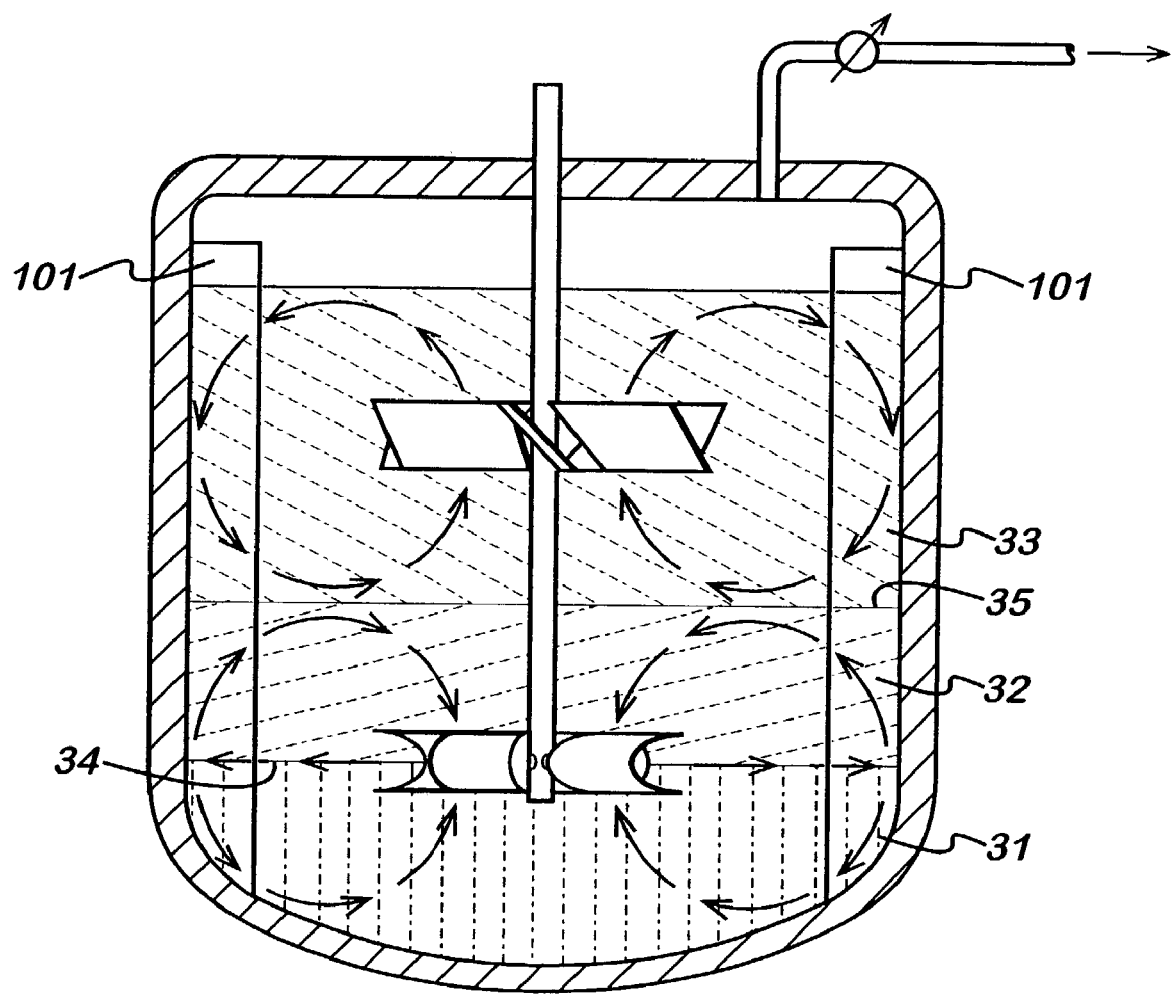
FIG. 4 shows the mixing zones defined by interfaces formed by local converging or diverging flow.

As shown schematically in FIG. 4, the configuration of the mixing elements of the reactor leads, in use, to three mixing zones. The three mixing zones consist of two lower mixing zones 31 and 32, one above and one below the lower impeller, and a third upper mixing zone 33 above and below the upper impeller. The mixing zones are defined by interfaces 34 and 35 formed by local converging or diverging flow. The mixing zones contain highly turbulent regions due to the nature of the flow. The region around the discharge of the upper mixing element and the lower mixing are particularly turbulent.

The contents of the reactor 1 are maintained at elevated temperature and pressure and with the oxidation reaction being exothermic heat is removed by allowing the volatile components of the oxidation reactor and particularly the solvent to vaporize. The corresponding vapor 6 is condensed 7 and most of the condensate is refluxed to the reactor 9 via inlets 10 thereby forming part of the liquid feed to the reactor, with some condensate being withdrawn 8 to control reactor water concentration. Details of this condensation process, which is typically carried out external to the oxidation reactor and the condensate stream control and split, are well known in the art.

EXAMPLES

Reduction in Impurities

Data exemplifying the present invention are given in Table 1 below. This data was obtained from the well established TAREACT computer model of the oxidation process. Example 1 shown in the table employs the Gasfoil (lower)/up-pumping pitch blade turbine (PBT) (upper) configuration of the invention, while Comparative Example 1 uses the known reactor configuration PBT (lower)/Rushton Turbine (RT) (upper) in use within the industry. Table 2 shows the mixing elements and feed configurations for these cases.

The configuration of Example 1 (Gasfoil/PBT) employs typical reactor conditions, as described within this document, that are standard in the art of p-xylene oxidation. P-xylene, catalyst and fresh and recycled solvent are fed to the liquid inlet in the proximity of the lower Gasfoil impeller.

Comparative Example 1 employs a vessel of similar dimensions to that of Example 1 but uses a two impeller configuration where the lower impeller is a PBT impeller and the upper impeller is a Rushton turbine. This is an impeller configuration in widespread use within the TPA manufacturing industry. P-xylene, catalyst and fresh and recycled solvent are fed to the liquid inlets in the proximity of the upper RT impeller. Gas is sparged to the oxidant inlet in the proximity of the PBT impeller. All other process conditions were identical to those of Example 1.

TABLE 1

Relative predictions of the catalyst requirement and the production rates of by products for the two reactor configurations.

| | Agitator | | Amounts of by-products relative to Comparative Example 1 | | | | | |
| --- | --- | --- | --- | --- | --- | --- | --- | --- |
| Example | Configuration Lower/Upper | Catalyst Requirement | Burn to COx | DCF | TMA | Benzoic Acid | Methyl Acetate | Methyl Bromide |
| Comparative Example 1 | PBT/RT | 1.00 | 1.00 | 1.00 | 1.00 | 1.00 | 1.00 | 1.00 |
| Example 1 | Gasfoil/ PBT | 0.98 | 1.00 | 0.65 | 0.99 | 0.67 | 0.95 | 0.95 |

Key:
PBT = up-pumping pitch blade turbine
RT = Rushton turbine
COx = carbon oxides (i.e. CO and $CO_2$)
DCF = dicarboxyfluorenone (a coloured species)
TMA = trimellitic acid

TABLE 2

Mixing Element and feed configurations of Example 1 and Comparative Example 1.

| Case | Agitator Configuration (Lower/Upper) | Number & location of air inlets | Number & location of pX & solvent inlets |
| --- | --- | --- | --- |
| Comparative Example 1 | PBT/RT | 2 above PBT | 2 @ RT |
| Example 1 | Gasfoil/PBT | 4 @ Gasfoil | 1 @ Gasfoil |

Vessels are of similar volumes and H/T.

Key:

H=operating (i.e. gassed) liquid depth,

T=vessel diameter, pX=p-xylene

Effect of Power Split on Reactor Performance

TAREACT model data (table 3) shows the deleterious effect of reducing the proportion of total power input by the PBT impeller in a gasfoil (lower)/PBT (upper) twin impeller configuration of the invention.

TABLE 3

Relative catalyst requirement and amounts of by-products obtained on changing the distribution of power between the upper and lower impellers in a gasfoil (lower)/PBT (upper) twin impeller configuration of the invention.

| PBT/Gasfoil power split | Burn to COx | DCF | TMA | Catalyst Requirement |
|---|---|---|---|---|
| 20:80 | 1.00 | 1.00 | 1.00 | 1.00 |
| 30:70 | 0.96 | 0.91 | 0.88 | 0.98 |
| 40:60 | 0.94 | 0.89 | 0.83 | 0.98 |
| 50:50 | 0.93 | 0.90 | 0.81 | 0.99 |

Modified Liquid & Gas Feed Points

TAREACT model data (table 4) shows the deleterious effect of positioning liquid feeds or oxidant inlets away from the high turbulence region of the gasfoil in a gasfoil (lower)/PBT (upper) twin impeller design. The "base" case had the liquid feeds and oxidant inlets in the high turbulence region of the gasfoil.

TABLE 4

Relative catalyst requirement and amounts of by-products obtained on changing the positions of the liquid inlets and the oxidant inlets in a gasfoil (lower)/PBT (upper) twin impeller configuration of the invention.

| Case | Burn to COx | DCF | TMA | Catalyst Requirement |
|---|---|---|---|---|
| Base | 1.00 | 1.00 | 1.00 | 1.00 |
| Liquid feeds below gasfoil | 1.00 | 1.00 | 0.97 | 1.00 |
| Liquid feeds above gasfoil | 1.01 | 1.05 | 1.06 | 1.01 |
| Oxidant inlets below gasfoil | 1.01 | 1.22 | 1.13 | 1.04 |
| Oxidant inlets above gasfoil | 1.03 | 1.15 | 1.05 | 1.02 |

Reduction in Reactor Wall Fouling

A titanium lined vertical cylindrical reactor approximately 2.7 m in diameter with dished ends was used to manufacture crude terephthalic acid from paraxylene. An acetic acid and water solvent, with a cobalt, manganese, bromide catalyst was used, as described above.

Two mixing element arrangements were tested using this system and the degree of solids build-up on the vessel walls was assessed with each agitation system. The initial agitation system consisted of a six blade radial impeller above a four blade up pumping mixed flow impeller. The second agitation system was as described in the detailed description of this invention. The thickness of solids build up on the vessel walls was inferred by measuring the reactor wall temperature and comparing this to the reactor contents temperature. For each agitation system, the reactor wall temperature was measured at four locations, using a thermal camera, for a period of over 20 days. The change in the temperature difference between the wall and contents temperature was recorded against time and is summarised in table 5 and shown in FIGS. 5 and 6.

TABLE 5

Change in temperature difference between average wall temperature and contents

| Agitation | Measuring Location | Change in temperature difference between average wall temperature and contents | | | | | | | | |
|---|---|---|---|---|---|---|---|---|---|---|
| | | Day 0 | Day 3 | Day 6 | Day 8 | Day 11 | Day 14 | Day 17 | Day 19 | Day 21 | Day 25 |
| Conventional Agitation | Location 1 | 0 | 1 | −1 | | 3 | 2 | 6 | 4 | 6 | |
| | Location 2 | 0 | 1 | −1 | | 0 | 2 | 7 | 5 | 5 | |
| | Location 3 | 0 | −1 | −3 | | 0 | 2 | 4 | 4 | 4 | |
| | Location 4 | 0 | 0 | −2 | | 0 | 1 | 5 | 5 | 4 | |
| | Average | 0 | 0.25 | −1.75 | | 0.75 | 1.75 | 5.5 | 4.5 | 4.75 | |
| DuPont Agitation System | Location 1 | 0 | | 0 | 1 | 0 | 0 | | | | 0 |
| | Location 2 | 0 | | 0 | 2 | 1 | 0 | | | | 3 |
| | Location 3 | 0 | | −1 | 1 | 2 | 2 | | | | 2 |
| | Location 4 | 0 | | 1 | 2 | 2 | 3 | | | | 4 |
| | Average | 0 | | 0 | 1.5 | 1.25 | 1.25 | | | | 2.25 |

The invention claimed is:

1. A reactor for the oxidation of a precursor to an aromatic carboxylic acid or ester thereof in a liquid phase reaction mixture, the reactor comprising an elongate baffled vessel, substantially vertical in use, having an upper mixing element and a lower mixing element, characterised in that the upper mixing element is an axial up-pumping impeller and the lower mixing element is a radial pumping impeller.

2. The reactor of claim 1 wherein the ratio of the swept diameter of the upper mixing element to the vessel diameter is from 0.3 to 0.7.

3. The reactor of claim 2 wherein the ratio of the swept diameter of the upper mixing element to the vessel diameter is from 0.4 to 0.6.

4. The reactor of claim 1 wherein the ratio of the submergence of the upper mixing element to the swept diameter is from 0.6 to 1.2.

5. The reactor of claim 1 wherein the ratio of the swept diameter of the lower mixing element to the vessel diameter is from 0.4 to 0.6.

6. The reactor of claim 5 wherein the ratio of the swept diameter of the lower mixing element to the vessel diameter is from 0.45 to 0.55.

7. The reactor of claim 3 or claim 6 wherein the ratio of the clearance of the lower mixing element from the base of vessel to the vessel diameter is from 0.1 to 1.0.

8. The reactor of claim 7 wherein the lower mixing element is a curved blade radial impeller which has parabolic blades with a plane of symmetry which is parallel to the plane of rotation.

9. The reactor of claim 1 or claim 8 wherein the upper mixing element imparts from 10 to 50% of the total power imparted by the upper mixing element, lower mixing element and any further agitator elements to the reaction mixture.

10. The reactor of claim 1 or claim 9 wherein the reactor comprises means for imparting through the agitator elements to the reaction mixture a power input of 2 to 15 kW per $m^3$ of reaction mixture.

11. The reactor of claim or claim 10 comprising an oxidant inlet having one or more inlet mouths for introducing an oxidant into the reactor, wherein the oxidant inlet mouth is disposed such that in use oxidant is introduced directly into a highly turbulent region of a mixing zone.

12. The reactor of claim 11 wherein the mixing zone is a lower mixing zone.

13. The reactor of claim 11 or claim 12 wherein the oxidant inlet mouth is located below the plane of the upper surface of the lower impeller.

14. The reactor of claim 13 wherein the oxidant inlet mouth is located such that the ratio of the distance between the swept diameter of the lower mixing element and the wall of the inlet mouth to the vessel diameter is in the range of ratio of 0.02 to 0.08.

15. The reactor of claim 14 comprising a liquid inlet having an inlet mouth for introducing a liquid feed of solvent, precursor and catalyst into the reactor.

16. The reactor of claim 15 wherein the liquid feed inlet mouth is disposed such that in use liquid feed is introduced into a region where reaction mixture is induced to flow into a mixing zone.

17. The reactor of claim 16 wherein the mixing zone is a lower mixing zone.

18. The reactor of claim 15 wherein the liquid inlet mouth is located between the plane of the upper surface of the lower impeller and the plane of the lower surface of the lower impeller, and between the swept diameter of the lower mixing element and the vessel wall.

19. The reactor of claim 15 wherein the liquid feed inlet mouth is disposed such that in use liquid feed is introduced into a region where reaction mixture is induced to flow via a mixing element into a highly turbulent region of a mixing zone.

20. The reactor of claim 19 wherein the liquid inlet mouth is located between the plane of the upper surface of the lower impeller and the plane of the lower surface of the lower impeller, and between the swept diameter of the lower mixing element and the vessel wall.

21. A process of oxidizing a precursor to an aromatic carboxylic acid or ester thereof in a liquid phase reaction mixture, comprising contacting one or more precursors of the aromatic carboxylic acid with an oxidant, in the presence of a catalyst and a liquid phase solvent, said contacting being effected in a reactor comprising an elongate baffled vessel, substantially vertical in use, having an upper mixing element and a lower mixing element, characterized in that the upper mixing element is an axial pumping impeller and the lower mixing element is a radial up pumping impeller.

22. The process of claim 21 wherein the aromatic carboxylic acid is terephthalic acid or isophthalic acid.

* * * * *